United States Patent
Morikawa et al.

(10) Patent No.: US 9,128,029 B2
(45) Date of Patent: Sep. 8, 2015

(54) X-RAY ANALYSIS APPARATUS

(71) Applicant: Rigaku Corporation, Akishima-shi (JP)

(72) Inventors: Keiichi Morikawa, Fuchu (JP); Hiroki Yoshida, Hino (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 165 days.

(21) Appl. No.: 13/648,525

(22) Filed: Oct. 10, 2012

(65) Prior Publication Data

US 2013/0136236 A1  May 30, 2013

(30) Foreign Application Priority Data

Nov. 24, 2011 (JP) ................................. 2011-256218

(51) Int. Cl.
*H05G 1/64* (2006.01)
*G01N 23/20* (2006.01)

(52) U.S. Cl.
CPC .......... *G01N 23/20* (2013.01); *G01N 2223/306* (2013.01)

(58) Field of Classification Search
CPC ....................................................... H05G 1/64
USPC ........................................................ 378/98.2
See application file for complete search history.

(56) References Cited

U.S. PATENT DOCUMENTS

| 7,120,227 B2* | 10/2006 | Ozawa et al. | 378/87 |
| 7,742,564 B2* | 6/2010 | Parham et al. | 378/71 |
| 2011/0126149 A1* | 5/2011 | Lalena et al. | 715/805 |

FOREIGN PATENT DOCUMENTS

JP            2008-57989 A       3/2008

* cited by examiner

*Primary Examiner* — Phillip A Johnston

(74) *Attorney, Agent, or Firm* — Buchanan Ingersoll & Rooney PC

(57) ABSTRACT

An X-ray analysis apparatus having a function for enabling a plurality of measurement methods to be implemented, the apparatus having: measurement software for implementing each of the individual measurement methods and acquiring measurement data; analysis software for performing a predetermined analysis on the measurement data and acquiring analysis data; reduced-size-image-creating means for creating a reduced-size image on the basis of each item of the measurement data and the analysis data; analysis-icon-creating means for creating an icon for denoting the analysis software; and image display means for displaying the reduced-size image and the icon on the same screen while indicating that the reduced-size image and the icon are correlated.

12 Claims, 6 Drawing Sheets

X-RAY ANALYSIS APPARATUS

BACKGROUND OF THE INVENTION

1. Field of the Invention

The present invention relates to an X-ray analysis apparatus having a function in which a plurality of measuring methods can be implemented.

2. Description of the Related Art

In recent years, there have been proposed X-ray analysis apparatuses having a function in which a plurality of measuring methods can be implemented. For example, according to Patent Citation 1, it is disclosed that X-ray diffraction measurement, X-ray small-angle scattering measurement, reflectivity measurement, and other measurement methods in which X-ray is used are performed using a single X-ray analysis apparatus.

(Patent Citation 1): JP-A 2008-057989

SUMMARY OF THE INVENTION

An apparatus in which it is possible to select a plurality of measurement methods and perform a variety of measurements, i.e., a so-called multifunctional apparatus, such as the X-ray analysis apparatus disclosed in Patent Citation 1, is exceptionally beneficial in being able to obtain a variety of measurement results using a single apparatus.

However, when the obtained measurement data, and analysis data obtained by analyzing the measurement data are displayed on a screen of a display in the form of file names and in the format of a list, the user has no means of knowing the type of data to which the measurement data or the analysis data corresponds or the nature of the software that performed the measurement or the analysis. This has been extremely inconvenient in terms of managing and reusing the data.

At present, the measurement data and the analysis data are typically stored as a file in a storage medium. In such an instance, the file name is usually appended with an extension. Ordinarily, the data type can be identified from the extension. However, in the field of X-ray analysis, items of data having the same extension may be obtained using different measurement methods. This is because the same measurement software caters for measurements performed using different methods. For example, with regards to wide-angle measurement data for a powdered sample and reflectivity measurement data for a thin-film sample, the types of measurement are different, but the same measurement software is used, and the extension is the same for both items of data. Therefore, relying only on the extension to estimate the type of data and determine the analysis software carries a risk of an error of judgment.

Purpose of Invention

With the above problem in conventional apparatuses in view, a purpose of the present invention is, with regards to an X-ray analysis apparatus capable of acquiring a plurality of types of measurement data and analysis data, to make it possible to ascertain data content, and analysis software estimated from the content, in a simple and accurate manner; and thereby make it possible to utilize data in a swift manner.

Configuration of the Invention

An X-ray analysis apparatus according to the present invention is an X-ray analysis apparatus having a function for enabling a plurality of measurement methods to be implemented, the X-ray analysis apparatus having: measurement software for implementing each of the individual measurement methods and acquiring measurement data; analysis software for performing a predetermined analysis on the measurement data and acquiring analysis data; reduced-size-image-creating means for creating a reduced-size image on the basis of each item of the measurement data and the analysis data; analysis-icon-creating means for creating an icon for denoting the analysis software; and image display means for displaying the reduced-size image and the icon on the same screen while indicating that the reduced-size image and the icon are correlated.

According to the present invention, even in an instance in which a plurality of items of measurement data and analysis data are displayed as an image on an image-display screen of the X-ray analysis apparatus, the user can see the reduced-size image and thereby establish the content of the data in a swift and accurate manner. The user can also see the icon and thereby establish the analysis software relating to the data in question in a simple and accurate manner. The user can also see the icon and thereby receive a suggestion with regards to the analysis software to be used in the next measurement. As described above, the present invention is extremely effective for performing data management for an X-ray analysis apparatus capable of implementing a plurality of measurement methods.

In the X-ray analysis apparatus according to the present invention, displaying the correlation between the reduced-size image and the icon involves displaying the icon adjacent to the reduced-size image, or having a portion of the icon overlap a portion of the reduced-size image in the display. Display configurations of such description make it possible to express the correspondence relationship between the reduced-size image and the icon in a simple and reliable manner.

In the X-ray analysis apparatus according to the present invention, it is preferable that the reduced-size image is displayed in accordance with image data created directly on the basis of the measurement data, rather than a regular-sized measurement-result image being created on the basis of the measurement data and subsequently performing a reduced-size display of the measurement-result image.

It is thus possible, e.g., to display the vertical axis as a logarithm or a root ($\sqrt{\ }$) in the reduced-size image, and is therefore convenient for displaying the result of an X-ray analysis. In the field of X-ray analysis apparatuses, measurement data or other data is sometimes displayed as a logarithmic scale or a $\sqrt{\ }$ scale; therefore, performing a reduced-size image display that accommodates such display formats makes it possible to speedily and accurately establish the analysis software, and is therefore convenient.

In the X-ray analysis apparatus according to the present invention, the analysis-icon-creating means can create the icon according to information inputted by the user. It is thus possible to present an analysis software in line with the approach of the user, and to perform an analysis in line with the user preferences.

In the X-ray analysis apparatus according to the present invention, the analysis-icon-creating means can identify the analysis software on the basis of an item notated in a file header portion of the measurement data, or an extension on the measurement data; or an item notated in a file header portion of the analysis data, or an extension on the analysis data. It is thereby possible to link the measurement data and the analysis software, or the analysis data and the analysis software, to each other in an accurate manner at all times; and to manage the data in a stable manner.

In the X-ray analysis apparatus according to the present invention, the analysis-icon-creating means can identify the analysis software on the basis of a notation of a measurement method ID entered in the file header portion of the measurement data or a notation of an analysis software ID entered in the file header portion of the analysis data.

In the field of X-ray analysis, measurement methods may be different between measurement data files having the same extension. If, with regards to measurement data of such description, the analysis software is identified on the basis of the extension as described above and an icon is created, there is a possibility that the judgment by the user will be imprecise. In particular, there is a possibility, in an instance in which the person performing data measurement and the person analyzing the measurement data are different, of it being necessary to perform additional work, such as appending file names with symbols designating the measurement means. In contrast, identifying the analysis software on the basis of a notation of measurement method IDs makes it possible to identify the analysis software in an accurate manner without burdening the person performing the measurement.

In the X-ray analysis apparatus according to the present invention, the analysis-icon-creating means can identify the analysis software on the basis of a measurement condition notated in the file header portion of the measurement data or a measurement condition notated in the file header portion of the analysis data.

Examples of the measurement condition include the type of measurement axis of a goniometer used for measurement, the scan range of incidence angles of an X-ray incident on the sample, or the range of scan rotation angles of the X-ray detector with respect to the sample. A configuration of such description makes it possible to determine the analysis software according to the measurement data or similar data.

DESCRIPTION OF THE PREFERRED EMBODIMENTS

Figure 1:
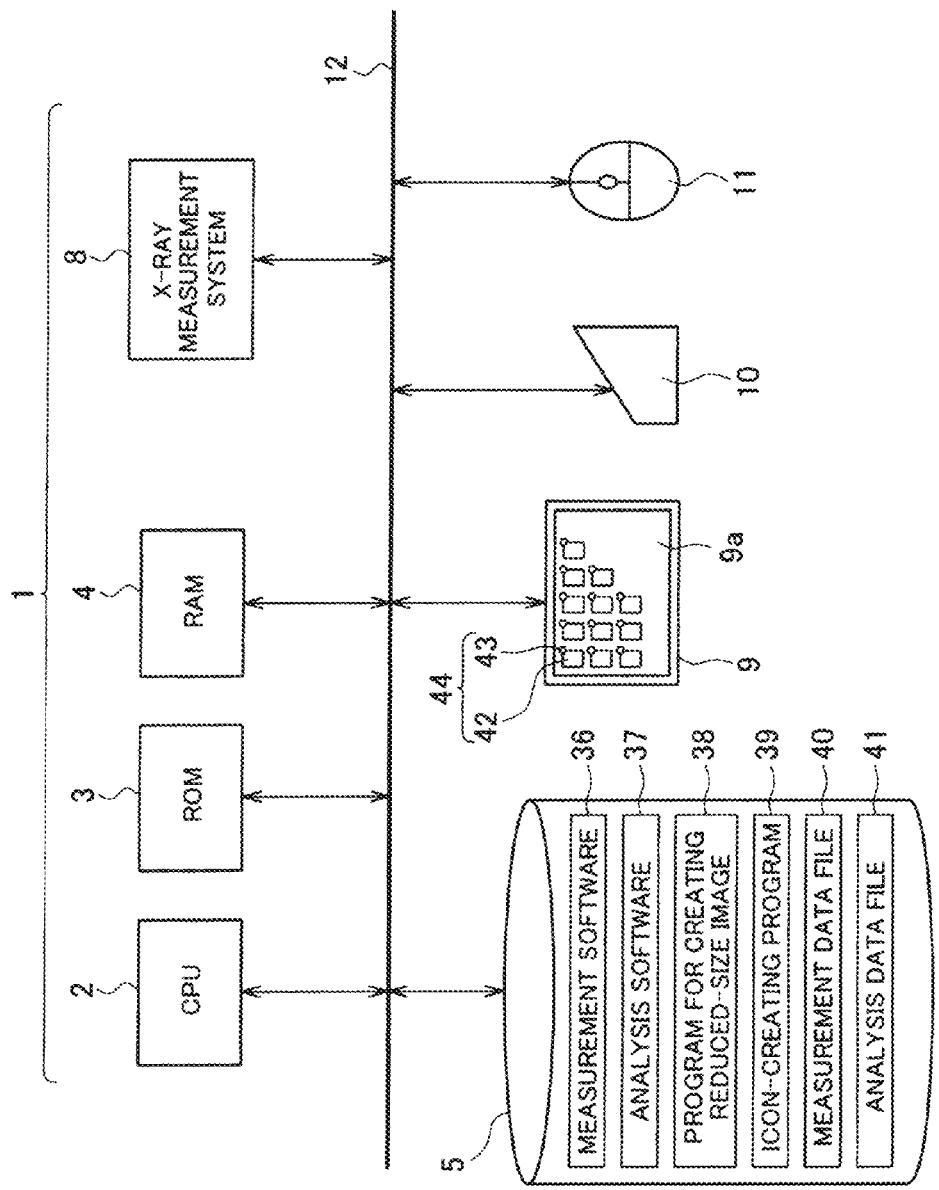
FIG. 1 illustrates an embodiment of an X-ray analysis apparatus according to the present invention.

The X-ray analysis apparatus according to the present invention will now be described on the basis of an embodiment. It shall be apparent that the embodiment is not provided by way of limitation to the present invention. In the drawings accompanying the present specifications, constituent elements may be shown at a proportion different to that in reality, so that characteristic portions are shown in a manner that is easily understood.

FIG. 1 shows an embodiment of the X-ray analysis apparatus according to the present invention. The X-ray analysis apparatus according to the present embodiment, the entirety of which is represented by numeral 1, has: a CPU 2, which is a central processing control device of the computer; a read-only memory (ROM) 3; a random-access memory (RAM) 4; and a memory unit 5, which is a storage medium. The ROM 3 and the RAM 4 form an internal memory of a computer.

The memory unit 5 comprises semiconductor memory, a hard disk, or another storage medium of choice. The memory unit 5 may be installed internally with respect to the computer, or may be installed externally with respect to the computer. The memory unit 5 may be a single unit, or may be a plurality of storage mediums. The CPU 2 implements predetermined functions according to programs stored in the memory unit 5 while accessing the ROM 3 and the RAM 4 as required.

The X-ray analysis apparatus 1 also has: an X-ray measurement system 8, which is a measurement mechanism for using X-ray and implementing a plurality of types of measurement methods; a display 9 corresponding to image display means for displaying an image; a keyboard 10 corresponding to input means; and a mouse 11, which also corresponds to input means. The above elements are connected to each other by a data bus 12.

Figure 2:
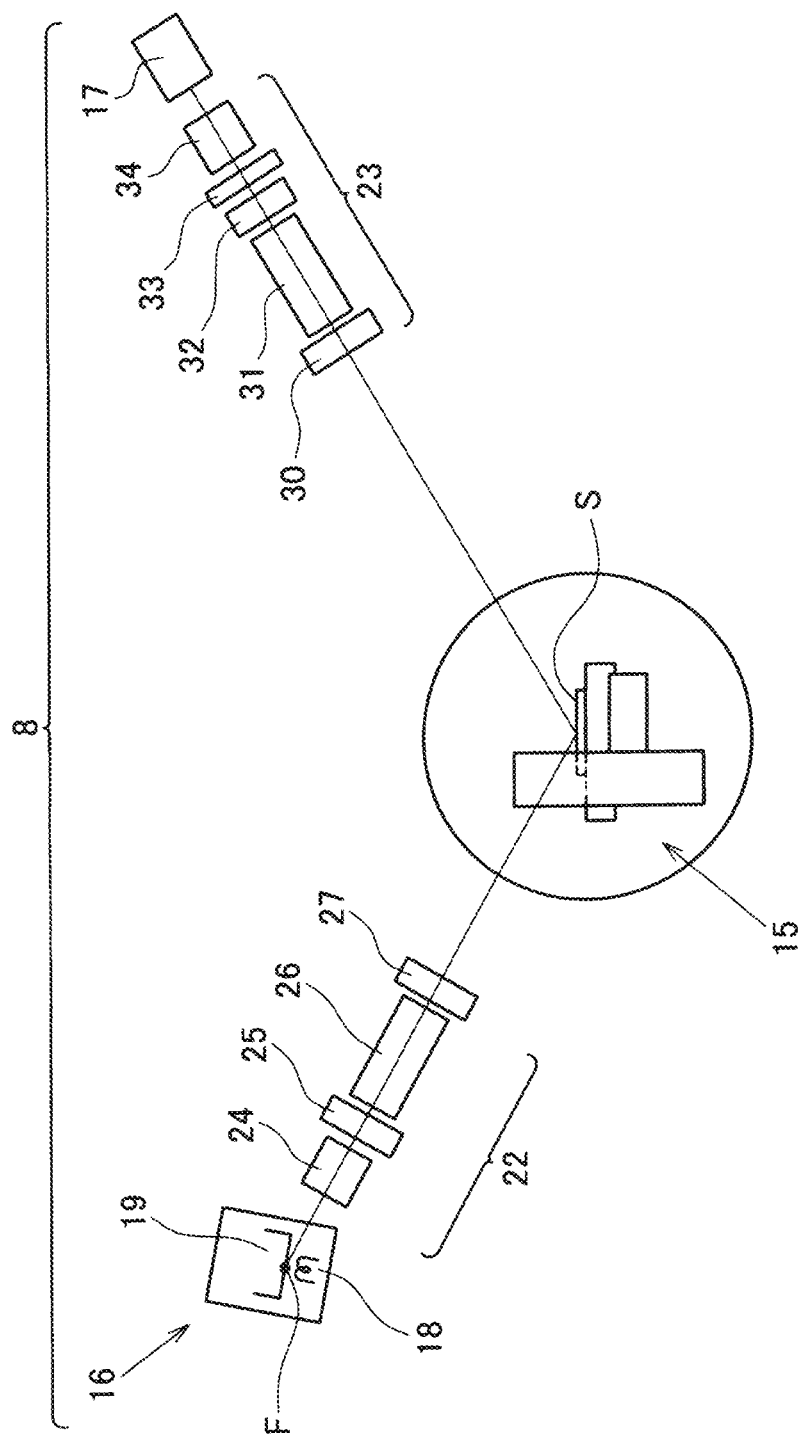
FIG. 2 illustrates an example of an X-ray measurement system, which is a principal section of the X-ray analysis apparatus shown in FIG. 1.

As shown in FIG. 2, in the present embodiment, the X-ray measurement system 8 has: a goniometer 15, which is an angle-measuring instrument; an X-ray generation device 16 installed on one side of the goniometer 15; and an X-ray detector 17 installed on the other side of the goniometer 15. A filament 18, which is a cathode; and a target 19, which is an anti-cathode, are provided to the interior of the X-ray generation device 16. A region at which electrons released from the filament 18 strike the surface of the target 19 is an X-ray focus F, and X-ray is generated from the X-ray focus F. In other words, the X-ray focus F functions as an X-ray source.

In the present embodiment, a 2-kW sealed tube in which a copper (Cu) target is used is used as the X-ray generation device 16. The X-ray focus F measures 1 mm×10 mm. An exiting X-ray beam may have a point-focus or a line-focus cross-sectional profile depending on requirement.

The X-ray detector 17 may be a zero-dimensional X-ray detector having no positional resolution ability; a one-dimensional X-ray detector having a positional resolution ability in a linear direction; or a two-dimensional X-ray detector having a positional resolution ability within a two-dimensional field. Examples of a zero-dimensional X-ray detector include a proportional counter or a scintillation counter. Examples of a one-dimensional X-ray detector include a position-sensitive proportional counter (PSPC) or a linear charge-coupled device (CCD) sensor. Examples of a two-dimensional X-ray detector include a two-dimensional CCD sensor, or a two-dimensional semiconductor sensor in which individual X-ray reception elements separately have an energy resolution ability.

An incident optical system 22 is provided between the X-ray generation device 16 and the goniometer 15. A reception optical system 23 is provided between the goniometer 15 and the X-ray detector 17. The incident optical system 22 has a monochromator unit 24, a cross-beam optics (CBO) unit 25, an incident optical unit 26, and an incident slit box 27.

A monochromator can be attached to or detached from the monochromator unit 24. It is possible to simply have a space with no monochromator being present. For the monochromator, a two-crystal monochromator Ge(220)×2, a two-crystal monochromator Ge(400)×2, a four-crystal monochromator Ge(220)×4, and a four-crystal monochromator Ge(440)×4 are selectively used.

Slits, comprising a focusing slit (BB), a parallel-beam slit (PB), a small-angle measurement slit (SA), and a microscopic measurement slit (MA), can be attached to or detached from the cross-beam optics unit 25. It is also possible to simply have a space with no slit being present.

A necessary slit can be attached to, and detached from, the incident optical unit 26. It is also possible to have a simple space with no slit being present. A plurality of types of Soller slits or in-plane parallel slit collimators (PSC) are selectively used as a slit.

A slit can be attached to, and detached from, the incident slit box 27, as necessary. It is also possible to have a simple space with no slit being present. Examples of the slits include a plurality of types, e.g., 5 types, of length-restriction slits within a range of, e.g., 0.5 mm to 15 mm.

The reception optical system 23 has a first reception slit box 30, a first reception optical unit 31, a second reception slit box 32, a second reception optical unit 33, and an attenuator unit 34. An appropriate filter (CuKβ filter in the present embodiment) can be attached to, and detached from, the first reception slit box 30. It is possible to have a simple space with no filter being present.

An appropriate analyzer can be attached to, and detached from, the first reception optical unit 31. It is also possible to have a simple space with no analyzer being present. A two-crystal analyzer Ge(220)×2 and a two-crystal analyzer Ge(400)×2 are selectively used as the analyzer. A plurality of types of parallel slit analyzers (PSAs) between which angles are different are also selectively used as the analyzer. As for the angle of the PSA, e.g., 1.0° and 0.5° are used.

A Soller slit and an in-plane parallel slit analyzer can be selectively attached to, and detached from, the second reception slit box 32. It is also possible to have a simple space with no slit or a similar element being present. For the Soller slit, e.g., Soller slit 5.0 deg and Soller slit 2.5 deg are used. As for the in-plane PSA, e.g., In-plane PSA 1.0 deg and In-plane PSA 0.5 deg are used.

A monochromator slit can be attached to and detached from, the second reception optical unit 33. It is also possible to have a simple space with no slit being present.

A counter monochromator can be attached to, and detached from, the attenuator unit 34. It is also possible to have a simple space with no counter monochromator being present. A curved monochromator or a flat monochromator is used as the counter monochromator.

Figure 3:
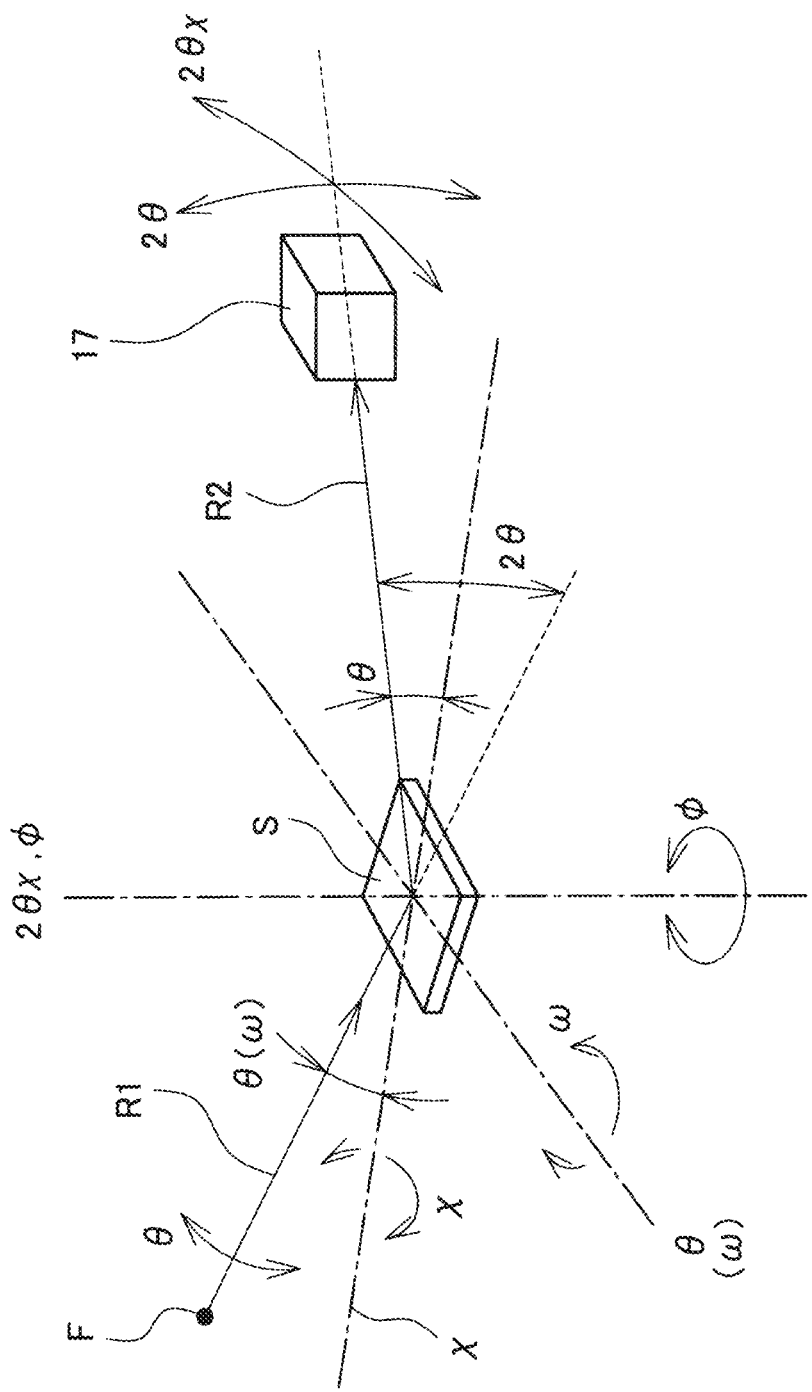
FIG. 3 schematically illustrates the scan axes and functions of a goniometer, which is a principal section of the X-ray analysis apparatus shown in FIG. 1.

The goniometer 15 is capable of implementing a plurality of measurement methods using a plurality of scan axes shown in FIG. 3. In FIG. 3, a sample S is placed at a predetermined position by a sample support device or a sample support platform (not shown). The sample support device or the sample support platform is a constituent element of the goniometer 15. In the present embodiment, the sample S is placed within a horizontal plane. The sample S may also be placed within a perpendicular plane.

In the present embodiment, the term "axial line," as in "θ-axial line," refers to the line itself, such as an imaginary line; and the term "axis," as in "θ-axis," refers to a support system for supporting a variety of components so as to be capable of rotation around the above-mentioned "axial line" or so as to be capable of movement along the "axial line."

1. Out-of-Plane Measurement

In FIG. 3, an X-ray source F is provided on one side of the position at which the sample S is placed. The X-ray source F is an X-ray focus formed on a surface of an anti-cathode (target) disposed opposite, e.g., a filament or another cathode. Specifically, a region at which electrons generated from the cathode strike the surface of the anti-cathode is an X-ray focus F, and X-ray is generated from the X-ray focus F. In the present embodiment, the X-ray focus is the X-ray source F.

Although X-rays are released from the X-ray focus F in all directions in three dimensions, X-rays released in a specific angular region exit to be emitted as an incident X-ray R1 onto the sample S. When crystal lattice planes in the sample S satisfy the Bragg's diffraction condition with respect to the incident X-ray R1, a diffracted X-ray R2 is generated from the sample S. In the present embodiment, the diffracted X-ray R2 is detected by the X-ray detector 17. A plane, shown in FIG. 3, that is within a space including the X-ray optical system and that includes the center line of the incident X-ray R1 and the center line of the diffracted X-ray R2 must coincide with a plane that is within the above-mentioned space and that includes the X-ray focus F and the X-ray detector 17.

In the present embodiment, a θ-axial line is set so as to pass through the surface of the sample S placed at a predetermined measurement position and so as to be parallel to the surface. The θ-axial line is set so as to be immobile. The θ-axial line also has a perpendicular relationship with the two above-mentioned imaginary planes. Rotationally moving the sample S relative to the X-ray source F about the θ-axial line makes it possible to vary the incidence angle θ of the incident X-ray R1 with respect to the sample S. Rotationally moving the X-ray source F relative to the sample S about the θ-axial line also makes it possible to vary the incidence angle θ. A rotational movement of such description of the X-ray source F or the sample S about the θ-axial line shall be referred to as a θ-rotation of the sample S.

Supposing that the diffracted X-ray R2 is generated when the X-ray is incident on the sample S at an incidence angle θ, the angle 2θ of the diffracted X-ray R2 with respect to the incident X-ray R1 (this angle 2θ shall hereafter be referred to as the "diffraction angle") will be twice the size of θ. The X-ray detector 17 rotationally moves about the θ-axial line so as to maintain an angle twice the size of the X-ray incidence angle θ, so that the diffracted X-ray R2 generated at diffraction angle 2θ can be detected. A rotational movement of such description of the X-ray detector 17 about the θ-axial line shall be referred to as a 2θ-rotation of the X-ray detector 17.

Thus causing the X-ray source F or the sample S to perform a θ-rotation about the θ-axial line, and causing the X-ray detector 17 to perform a 2θ-rotation about the θ-axial line in synchronization, is referred to as a "2θ/θ-scan." The expression "A/B" (where each of A and B represents an operating axis) indicates that the motion of A and the motion of B are coupled, i.e., interlinked.

A plane including the center line of the incident X-ray R1 incident on the sample S and the center line of the diffracted X-ray R2 from the sample S is generally called an equatorial plane, or out-of-plane. A measurement method in which the X-ray source F is caused to undergo a θ-rotation and the X-ray detector 17 is simultaneously caused to perform a 2θ-rotation on this plane, and data is acquired, is called out-of-plane measurement. The measurement performed in the present embodiment, in which the X-ray source F and the X-ray detector 17 are caused to perform a 2θ/θ-scan, is a form of out-of-plane measurement.

2. In-Plane Measurement

In FIG. 3, there is set a 2θχ(theta-chi) axial line, which perpendicularly penetrates the sample S placed at the predetermined sample position and orthogonally intersects the immobile θ-axial line. If the θ-axial line is a horizontal line, the 2θχ-axial line is a perpendicular axial line; and if the θ-axial line is a perpendicular axial line, the 2θχ-axial line is a horizontal axial line. There is also set a φ-axial line, which is an axial line that orthogonally intersects the surface of the sample S placed at the predetermined sample position. In FIG. 3, the φ-axial line and the 2θχ-axial line overlap and form a single line. However, while the 2θχ-axial line is an immobile line, the φ-axial line is an axial line that moves in correspondence with the movement of the sample S when the sample S moves in a swinging or an slanted motion.

A direction orthogonally intersecting the 2θχ-axial line and being on a plane that includes the surface of the sample S and that is at a right angle with respect to the equatorial plane, which includes the center line of the incident X-ray R1 incident on the sample S and the center line of the diffracted X-ray R2 from the sample S, is generally called an "in-plane" direction. In the present embodiment, there is provided a driving system for rotationally moving the X-ray detector 17 around the 2θχ-axial line. The driving system rotationally moving the X-ray detector 17 around the 2θχ-axial line makes it possible to move the X-ray detector 17 in the in-plane direction. A movement of the X-ray detector 17 in the in-plane direction of such description is called a 2θχ-scan.

In the present embodiment, there is provided a driving system for rotationally moving the sample S around the φ-axial line, which orthogonally intersects the sample S itself. Rotationally moving the sample S around the φ-axial line is generally called a φ-scan. The rotation of the sample S within a two-dimensional field, caused by the φ-scan, is generally called intra-planar rotation of sample S.

Combining causing the sample S to perform a φ-scan and causing the X-ray detector 17 to perform a 2θχ-scan make it possible to obtain useful X-ray diffraction data relating to the sample S. A measurement method of such description is generally called in-plane measurement.

3. Rocking Curve Measurement (ω-Scan)

A rocking curve is a diffraction intensity curve measured when an X-ray beam having a high monochromacity and parallelism is made incident on a sample crystal, and the angle of incidence of the X-ray with respect to the sample is slowly rotated at a constant low speed in the vicinity of an angle satisfying the Bragg's diffraction condition. Normally, this curve is drawn on a graph in which the horizontal axis represents the angle of X-ray incidence and the vertical axis represents the X-ray intensity.

In the out-of-plane measurement described above, with regards to FIG. 3, the angle θ of the X-ray R1 incident on the sample S from the X-ray source F (i.e., the X-ray incidence angle θ) is in a 1:2 relationship with the angle 2θ of the diffracted X-ray R2 with respect to the incident X-ray R1, and the X-ray source F and the X-ray detector 17 are in positions that are symmetrical to each other with respect to a perpendicular plane of the sample S.

On the other hand, in an instance in which the X-ray incidence angle θ is in a 1:2 relationship with the angle 2θ of the diffracted X-ray R2 with respect to the incident X-ray R1, but the X-ray source F and the X-ray detector 17 are not in positions that are symmetrical to each other with respect to a perpendicular plane of the sample S, the angle that the incident X-ray R1 forms with respect to the sample surface is called "angle ω." In the present embodiment, in an instance in which the angle, with respect to the sample surface, of the X-ray R1 incident from the X-ray source F to the sample S, and the angle, with respect to the sample surface, of the diffracted X-ray R2 are not in a relation of symmetry with each other, the θ-axial line is referred to as a ω-axial line, the θ-axis is referred to as an ω-axis, and a θ-scan is referred to as an ω-scan.

Securing the position of the X-ray source F and the X-ray detector 17 at an angle that satisfies the Bragg's diffraction condition of the sample crystal, and performing a ω-scan on the sample S around the ω-axial line as described above, make it possible to obtain a mountain-shaped or a peak-shaped diffraction intensity diagram, i.e., rocking curve. A measurement method thus performed is called rocking curve measurement by ω-scanning.

4. Rocking Curve Measurement (φ-Scan)

With regards to FIG. 3, securing the position of each of the X-ray source F and the X-ray detector 17 at an angle that satisfies the Bragg's diffraction condition of the sample crystal, and performing a φ-scan on the sample S around the φ-axial line, make it possible to obtain a mountain-shaped or a peak-shaped diffraction intensity diagram, i.e., a rocking curve. A measurement method thus performed is called rocking curve measurement by φ-scanning.

5. High-Resolution Rocking Curve Measurement (2θ/ω-Scan)

With regards to FIG. 3, a measurement method for obtaining the rocking curve of crystal lattices having a tilt of angle α with respect to the surface of the sample S is a method in which a 2θ/ω-scan is performed on the sample S in a state in which the position of the X-ray detector 17 is set based on a relationship in which angle α is added to angle θ, and the resulting angle is used as the X-ray incidence angle ω, and in which angle α is subtracted from angle 2θ at the same time, angle θ being one at which the Bragg scattering conditions of the sample crystal are satisfied. It is thereby possible to obtain a mountain-shaped or a peak-shaped diffraction intensity diagram, i.e., rocking curve, at a high resolution.

6. High-Resolution In-Plane Measurement

With regards to FIG. 3, emitting the incident X-ray R1 at the surface of the sample S at an angle in the vicinity of the total reflection critical angle, and causing the sample S to perform a 2θχ/φ-scan at an angle satisfying the Bragg's diffraction condition of the sample crystal having a normal parallel to the surface of the sample S, make it possible to perform a high-resolution in-plane measurement.

7. Thin-Film Measurement

With regards to FIG. 3, securing the X-ray incidence angle ω with respect to the sample S to a small angle of no greater than several degrees (e.g., no greater than 3°), and causing the X-ray detector 17 to perform a 2θ-scan and measuring the diffracted X-ray, make it possible to measure the diffracted X-ray generated by a thin film formed on a substrate. A measurement method performed as described above is called thin-film measurement.

8. Pole Figure Measurement

Generally, an intersection between a sphere having the crystal as the center (i.e., a projection sphere) and a normal of a lattice plane of the crystal is known as a pole. A diagram obtained on a polar net shown in FIG. 4, which represents plane coordinates, by performing a stereo projection, i.e., a stereographic projection, of the projection sphere on the polar net is a pole figure.

Figure 4:
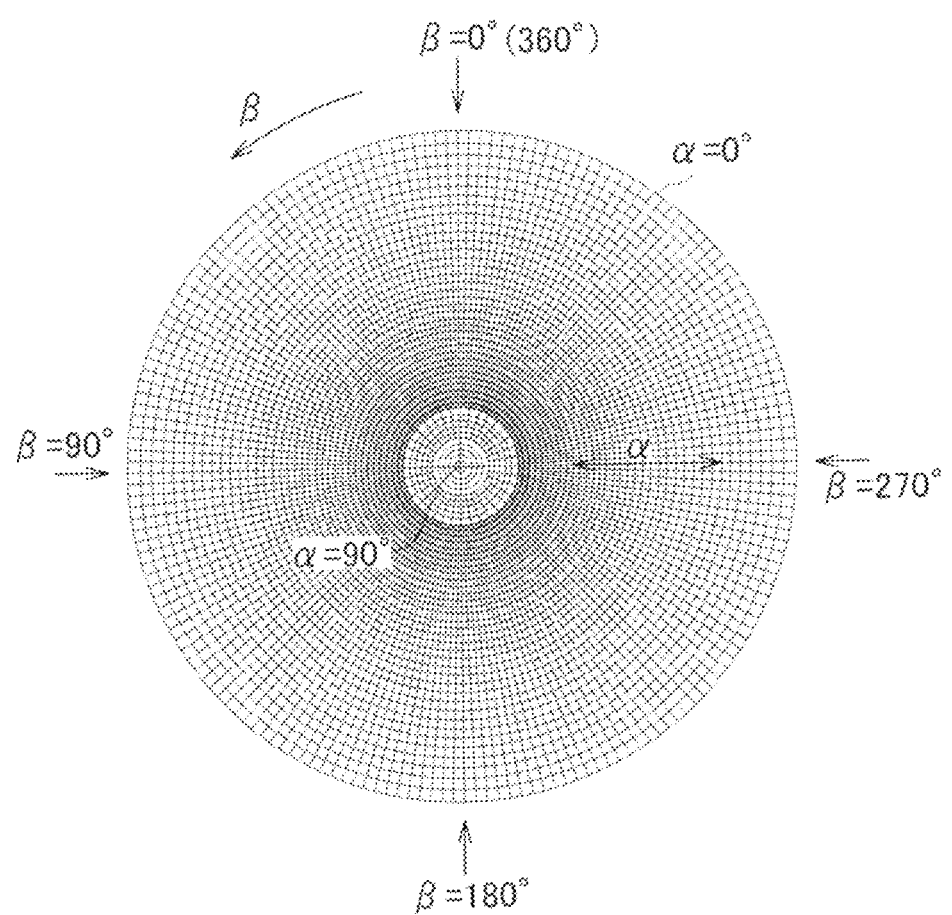
FIG. 4 illustrates an example of a polar net used to achieve one of the functions of the goniometer.

The pole figure is sometimes called a pole diagram. Using this pole diagram makes it possible to display, in an appropriate manner, the orientation state of a polycrystal, i.e., the crystal orientation in a polycrystal. The polar net shown in FIG. 4 represents polar coordinates in which the radial direction represents the angle α (°) and the circumferential direction represents the angle β (°).

The above-mentioned pole diagram can be measured, e.g., as follows. Specifically, with regards to FIG. 3, angle θ of incidence of the X-ray R1 with respect to the sample S and angle 2θ of the diffracted X-ray R2 with respect to the incident X-ray R1 are secured to the angle satisfying the Bragg's diffraction condition of the sample crystal. Then, while the angle (i.e., tilt angle) χ of the sample S around a χ-axial line, which is an axial line passing through the surface of the sample S placed on a predetermined sample position and orthogonally intersecting both the θ-axial line and the 2θχ-axial line, and the intra-planar rotation angle φ of the sample S around the φ-axial line, are caused to vary, a measurement is made for the intensity I of the diffracted X-ray at individual sample positions specified by the tilt angle χ and the intra-planar rotation angle φ. Polar data specified by (χ, φ, I) is thereby measured.

Next, a predetermined conversion equation is used to convert a χ-value to an α-value, a predetermined conversion equation is used to convert a φ-value to a β-value, and polar data specified by (α, β, I) is obtained. The (α, β, I) polar data obtained is plotted on the polar net shown in FIG. 4, whereby a pole figure can be obtained. Pole figure measurement thus performed is the method that is commonly used.

Pole figure measurements are not limited to a pole figure measurement such as that described above. For example, in JP-A 2001-056304, there is disclosed performing a correction on data obtained by in-plane measurement previously mentioned to obtain a pole figure. A pole figure measurement thus performed is called an in-plane pole figure measurement.

9. Reciprocal Space Map Measurement (ω-Steps, 2θ/ω-Scan)

A reciprocal space map is a diagram showing the intensity distribution of diffracted X-ray from a sample crystal plane in a reciprocal space. A reciprocal space is, as is well known, a space formed by reciprocal lattice vectors; and is one in which the periodicity of real space is reflected. A reciprocal lattice vector is, as is well known, a vector defined by a predetermined relationship with a fundamental vector of a crystal in real space. In general, a reciprocal lattice point exists at the tip of a reciprocal lattice vector, and a plurality of reciprocal lattice points are arranged in an ordered manner in the reciprocal space.

By creating and observing this reciprocal space map, it is possible to find out, e.g., fluctuations in the lattice constant of the crystal, the degree of mosaic structure of the lattice plane, and similar parameters.

In the present embodiment, in the measurement of a reciprocal lattice point of interest, the sample S is moved to an angle (2θ, ω) that satisfies the Bragg's diffraction condition, and a 2θ/ω-scan is executed at each ω-position while moving the sample S to positions at which the ω-angle of the sample S is incrementally increased or decreased by Åω with each step. Summing the number of steps by which the sample S has moved by Δω, repeatedly executing the 2θ/ω-scan, and measuring a plurality of data make it possible to obtain an intensity distribution map on coordinates in which the horizontal axis represents Åω and the vertical axis represents 2θ/ω, i.e., a reciprocal space map.

10. Reciprocal Space Map Measurement (φ Steps, 2θ/ω-Scan)

In the in-plane measurement described above, the sample S is caused to perform a φ-scan and the X-ray detector 17 is caused to perform a 2θχ-scan in an interlinked manner, whereby in-plane measurement is implemented. Also, in the reciprocal space map measurement based on ω-steps mentioned above in section 9, a 2θ/ω-scan is performed, whereby reciprocal space map measurement is implemented. With regards to the reciprocal space map measurement based on ω-steps described in section 9, replacing the 2θ-axis with the 2θχ-axis, replacing the ω-axis with the φ-axis, and performing a 2θω/φ-scan make it possible to execute a reciprocal space map measurement in the in-plane direction, i.e., a reciprocal space map measurement based on φ-steps.

11. Wide-Region Reciprocal Space Map Measurement

With regards to FIG. 3, the sample S is moved in incremental steps of Δχ, and a 2θ/ω-scan is executed. Summing the number of steps by which the sample S has moved by Δχ, repeatedly performing the 2θ/ω-scan, and measuring a plurality of data make it possible to obtain an intensity distribution map on coordinates in which the horizontal axis represents Δχ and the vertical axis represents 2θ/ω.

In the reciprocal space map measurement based on ω-steps described in section 9, the diffracted X-ray intensity is measured while moving the ω-axis, and the reciprocal space map is obtained. According to this method, there is a restriction in relation to the movement of the ω-axis, and the measurement range is therefore restricted. In contrast, using the movement of the χ-axis as with the present measurement involves no restriction on the amount of movement, and therefore makes it possible to perform a reciprocal space map measurement over a wide region. In other words, it becomes possible to perform measurement in relation to a reciprocal space over a wide range.

12. Reflectivity Measurement

The refractive index of a substance in relation to X-ray is slightly smaller than 1; and if X-ray is incident on a substance at an extremely shallow angle, total reflection will occur. The X-ray reflectivity can be obtained by measuring the X-ray reflection intensity in the vicinity of an angular position at which total reflection occurs (i.e., in the vicinity of total reflection). The depth of X-ray entry into a substance in the vicinity of total reflection is extremely small, at about 10 to 100 nm from the surface, and X-ray reflectivity measurement is effective for, e.g., structural evaluation in the vicinity of the surface of a substance or structural evaluation of a thin film.

When performing a reflectivity measurement, the range of the angle θ of incidence of X-ray on the sample S is set to a minute-angle region of, e.g., about θ=0.05° to 4°, and a 2θ/θ scan is performed to detect the resulting reflected X-ray using the X-ray detector. In this reflectivity measurement device, subjecting the sample S to X-rays that have been precisely monochromatized; selecting, from the X-rays emerging from the sample S, only those X-rays that satisfy a predetermined angular resolution; and supplying only the selected X-rays to the X-ray detector, make it possible to obtain reflectivity data having a high degree of reliability.

In the present embodiment, a 2θ/θ-scan is performed, i.e., a 2θ-scan and a θ-scan are executed in an interlinked manner, whereby the reflectivity is measured.

13. Small-Angle Scattering Measurement

In some substances, when X-rays are emitted at the substance, X-ray scattering may be generated at a small-angle region, e.g., an angular region of about 2θ=0° to 5°, around the optical axis of the incident X-ray. For example, if fine particles of about 10 to 1000 Å or regions having a corresponding size in which the density is uneven are present in the substance, scattering that is diffuse, or so-called diffuse scattering, occurs in the direction of the incident X-ray. In this diffuse scattering, the spread of the scattering increases with decreasing particle size, irrespective of the internal structure of the particles. In the present embodiment, causing the X-ray detector 17 to perform a 2θ-scan makes it possible to perform small-angle scattering measurement. Disposing the X-ray detector 17 on the side of the X-ray-irradiated surface of the sample S makes it possible to perform a reflection small-angle scattering measurement; and disposing the sample S in a perpendicular manner so as to transmit incident X-ray, and disposing the X-ray detector 17 on an opposite side of the sample S to the X-ray-irradiated surface, make it possible to perform a transmission small-angle scattering measurement.

(Arithmetic Control System)

In FIG. 1, a variety of program software, files, and other data are stored in regions, each having the respectively necessary capacity, in the memory unit 5. In the drawing, for purposes of convenience, the items of software, files, and similar data are shown in a single memory unit. However, these items of program software may be divided and stored in a plurality of storage mediums according to necessity.

Specifically, measurement software 36, analysis software 37, a program 38 for creating a reduced-size image, an icon-creating program 39, a measurement data file 40, and an analysis data file 41 are individually stored in a predetermined region of the memory unit 5.

The measurement data file 40 is a region for storing measurement data acquired by a variety of measurements executed by a variety of measurement software. The measurement data is raw data obtained by measurement. The analysis data file 41 is a region for storing analysis data acquired by a variety of analyses executed by a variety of analysis software.

The measurement software 36 is software for implementing, using the X-ray measurement system 8 shown in FIG. 2, out-of-plane measurement, in-plane measurement, rocking curve measurement, thin-film measurement, pole figure measurement, reciprocal space map measurement, reflectivity measurement, small-angle scattering measurement, and a variety of measurement methods used as required.

The analysis data is data obtained by applying some sort of an analysis, i.e., processing, on the measurement data. Examples of the analysis include background correction, peak correction, smoothing, peak search, qualitative analysis performed through a comparison with a database, and quantitative analysis.

(Analysis Software)

The analysis software 37 is program software for causing the CPU 2 to implement a predetermined function in order to perform an analysis on measurement data obtained by a variety of measurement methods. Specifically, the analysis software 37 is analysis software such as that shown, e.g., in the following Table 1.

TABLE 1

| FILE PART ID | Measurement type | Corresponding analysis software |
| --- | --- | --- |
| MEAS_KHP2_00055 | Reflectivity measurement | GlobalFit |
| MEAS_KHP2_00056 | Rocking curve measurement | GlobalFit |
| MEAS_KHP2_00058 | Reciprocal space map measurement | 3D Explore |
| MEAS_KHP2_00062 | Wide-angle measurement (focusing method) | PDXL |
| MEAS_KHP2_00063 | Small-angle scattering measurement | NANO Solver |

The analysis software 37 shown in Table 1 may be "Global Fit," which is software for performing an analysis on measurement data obtained by reflectivity measurement and rocking curve measurement; "3D Explore," which is software for performing an analysis on measurement data obtained by reciprocal space map measurement; "PDXL," which is software for performing an analysis on measurement data obtained by wide-angle measurement; "NANO Solver," which is software for performing an analysis on measurement data obtained by small-angle scattering measurement; or similar software.

Each of the measurement methods is affixed with an ID used in the program software. Specifically, each of the reflectivity measurement, rocking curve measurement, reciprocal space map measurement, wide-angle measurement, and small-angle scattering measurement is respectively affixed with IDs: MEAS_KHP2_00055, MEAS_KHP2_00056, MEAS_KHP2_00058, MEAS_KHP2_00062, and MEAS_KHP2_00063.

The above example is an example of measurement methods and analysis software. In reality, it is possible to employ analysis software for implementing a larger number of types of measurement methods depending on necessity. Also, while Table 1 shows an example in which an ID is given to each of the measurement methods, an ID may also be given to each item of analysis software instead of the measurement methods.

(Program for Creating a Reduced-Size Image)

The program 38 for creating a reduced-size image is program software for creating an image having a size, smaller than regular size, that is suitable for displaying in list format, in relation to the measurement data acquired by the variety of measurement methods described above and the analysis data acquired by the variety of analysis programs mentioned above. It shall be apparent that program software for creating a regular-sized image is also provided in a storage medium of choice; however, an illustration thereof is not provided in FIG. 1.

The "regular size" may refer to a size substantially identical to the screen size of the display 9 in FIG. 1; or, in an instance in which an appropriately sized image box (i.e., a window) is displayed on the screen of the display 9, may refer to a size substantially identical to the image box. Reduced-size images refer to individual images in an instance in which a plurality of images which are reduced in size are displayed, within a regular screen size of such description, at a predetermined arrangement, e.g., as a line or in a random manner.

Figure 5A:
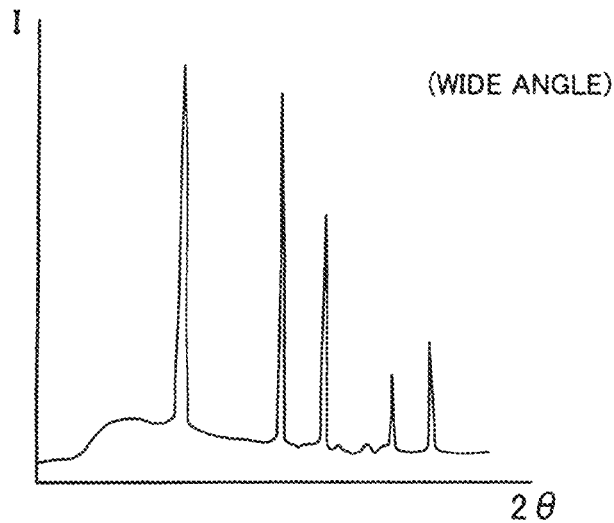
FIGS. 5A and 5B illustrate an example of measurement data or analysis data.

Generally, when measurement data or analysis data obtained by performing a wide-angle measurement on a powdered sample is displayed as an image using a graph, an image such as that shown in FIG. 5A is obtained. The graph shown here is a graph in which the vertical axis represents the X-ray intensity (I) and the horizontal axis represents the diffraction angle (2θ). Since the graph corresponds to a wide-angle measurement, a large angular range is present for 2θ.

Figure 5B:
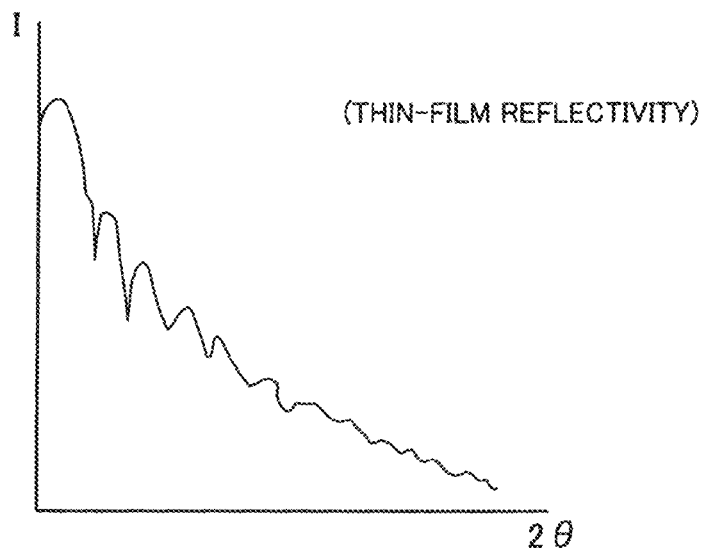

FIG. 5B is an example showing an instance in which measurement data or analysis data obtained by performing a reflectivity measurement on a thin-film sample is displayed as an image using a graph. The graph shown here is also a graph in which the vertical axis represents the X-ray intensity (I) and the horizontal axis represents the diffraction angle (2θ). Since the graph corresponds to a reflectivity measurement, the angular range of the diffraction angle 2θ is narrower, and corresponds to smaller angles, than that for the wide-angle measurement.

Figure 6:
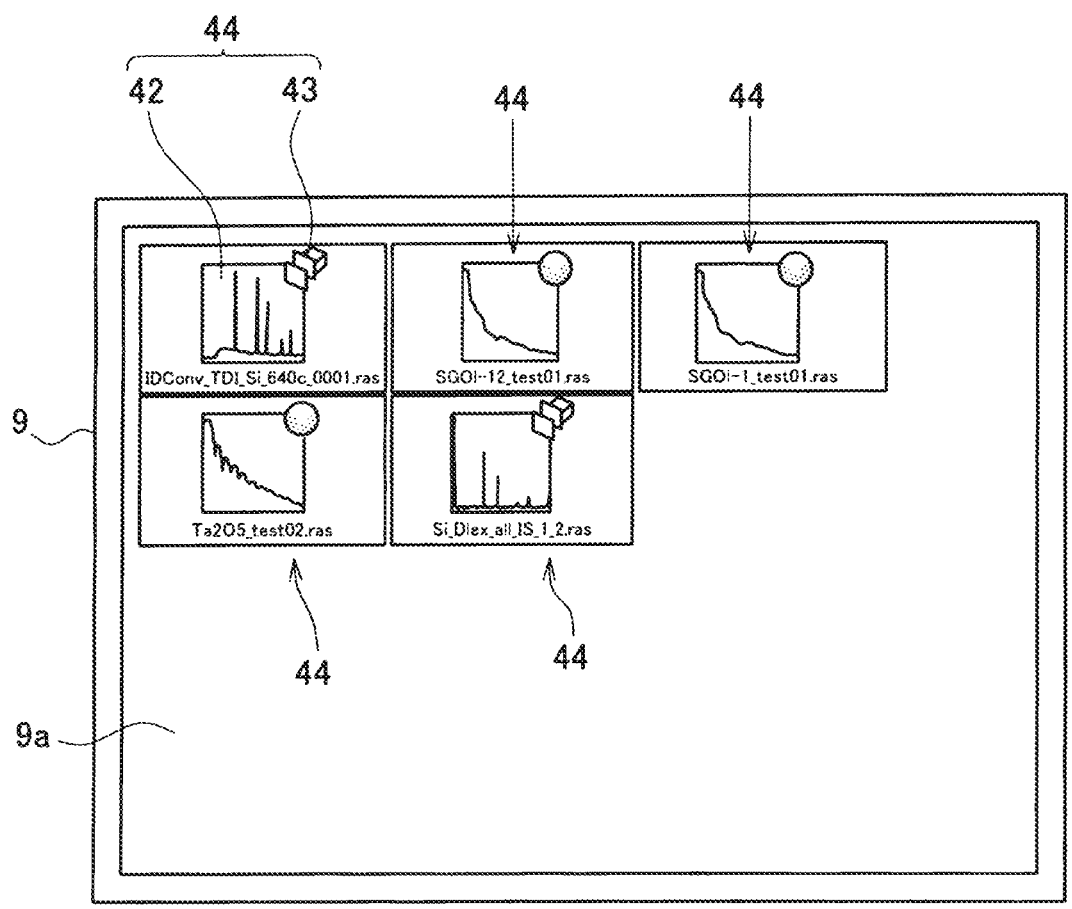
FIG. 6 illustrates examples of reduced-size images and icons according to the present invention.

An X-ray analysis apparatus 1 of the present embodiment is capable of displaying measurement data and analysis data as a list as shown, e.g., in FIG. 6, on a display screen 9a of the display 9. It shall be apparent that software for performing this list display is also necessary; however, an illustration of this software is not provided in FIG. 1.

The list display shown in FIG. 6 is configured by displaying a plurality of joint images 44, each comprising a reduced-size image 42 and an icon 43 (described further below), so that the joint images 44 are arranged in vertical and horizontal rows and columns. The program 38 for creating a reduced-size image shown in FIG. 1 is software for creating the reduced-size images 42 of the above-mentioned joint images 44. The program 38 for creating a reduced-size image, uses e.g., the following two methods to create the reduced-size image 42 on the basis of measurement data or analysis data forming the basis of the regular-sized display of measurement results shown in FIGS. 5A and 5B.

The first method is to use a predetermined size-reduction algorithm to perform size-reduction processing on a regular-sized display of measurement results shown in FIGS. 5A and 5B. The second method is to use a predetermined reduced-side-image-creating algorithm to create new image data corresponding to a reduced-size image from measurement data or analysis data forming the basis of the regular-sized display of measurement results shown in FIGS. 5A and 5B.

In carrying out the present invention, either the first or the second method can be employed. However, considering an instance in which the method is applied particularly to an X-ray analysis apparatus, the second method is thought to be preferable. This is because with regards to observation of measurement data or the like in an X-ray analysis apparatus, when an observation is made using a graph such as that shown in FIG. 5A, there are instances in which an analysis is easier to perform if the vertical axis is displayed as a logarithm or a root ($\sqrt{}$); and the second method (i.e., the method for generating an image data for a reduced-size image) is preferable in order to cater for this requirement.

In FIG. 6, the code affixed to the lower position of each of the joint images 44 represents the file name of the measurement data or the analysis data. In the example shown, the extension of all files is the same, being ".ras"; however, it shall be apparent that if there is a difference in the measurement method or the analysis method, the affixed extension will be different.

(Icon-Creating Program)

The icon-creating program 39 shown in FIG. 1 is software for creating the icons 43 of the joint images 44 in FIG. 6. An icon 43 is a symbol denoting the analysis software that the measurement data or the analysis data indicated by the reduced-size image 42 corresponds to. More specifically, the icon 43 can provide the user with information such as an indication of the analysis software used to obtain the data forming the basis of the corresponding reduced-size image 42, or a suggestion (namely, a pointer) of the analysis software to be used next time the data forming the basis of the reduced-size image 42 is to be handled.

The design of the icon 43 is determined in advance in correspondence with each piece of analysis software. A setup is present so that the design of the icon 43 is different between different analysis software. In the present embodiment, the icon 43 is decided on the basis of a notation in the header section of the file containing the measurement data or the analysis data, or determined according to the file name extension corresponding to the measurement data.

Examples of methods for deciding the type of icon 43 on the basis of a notation in the header section of the file include, e.g., noting the ID number allocated to each analysis software, shown in the above-mentioned Table 1, into the header section in advance, and reading the ID number and identifying the analysis software; or reading a condition under which the measurement data or the analysis data are acquired (e.g., the measurement range of the diffraction angle 2θ, the range of the angle of incidence of X-ray onto the sample, the type of optical component used, etc.) and identifying the analysis software.

For example, as shown in the following Table 2, it is possible to read the ID number notated in a predetermined row (row 9 in Table 2) of the header section of the file (RAS-format data file in the case of this table). In Table 2, an ID number of the measurement method is used as the ID number. However, it is also possible to affix ID numbers to analysis software, and employ the ID number of the analysis software as information in the header section.

TABLE 2

| (Row 1)  | *FILE_COMMENT " " |
| (Row 2)  | *FILE_MD5 " " |
| (Row 3)  | *FILE_MEMO " " |
| (Row 4)  | *FILE_OPERATOR "morikawa" |
| (Row 5)  | *FILE_SAMPLE " " |
| (Row 6)  | *FILE_TYPE "RAS_RAW" |
| (Row 7)  | *FILE_USERGROUP "system manager" |
| (Row 8)  | *FILE_VERSION "1.0000000000" |
| (Row 9)  | *FILE_PART_ID "MEAS_KHP2_00055" |
| (Row 10) | *HW_ATTACHMENT_ID "ATT0021" |
| (Row 11) | *HW_ATTACHMENT_NAME "XY-20mm|XY-20mm" |

More specifically, the type (namely, design) of icon 43 on the reduced-size image 42 can be determined as follows.

(1) The user can determine the type of icon 43 through a keyboard, a mouse, or another input device. This makes it possible to display an icon in line with the user's measurement approach. It also makes it possible to freely determine, in accordance with the user's aim, the suggestion function in relation to the next time the analysis process is performed.

(2) The type of icon 43 can be determined by the computer on the basis of measurement conditions or analysis conditions notated in the header section or another section of the file. Human errors can thus be avoided.

(3) The type of icon 43 can be determined by the computer on the basis of the file extension. In an X-ray analysis apparatus, the details of measurement may differ even if the extension is the same. Therefore, in this instance, it is preferable that a measure such as referencing the information in the header section be taken.

(4) In an instance in which the user has used a different analysis software to that used in the previous occasion for the measurement data or the analysis data in question, the icon 43 can be switched to that corresponding to the analysis software that is used. It is thus possible to perform an analysis in line with the user's approach.

(Operation of the X-Ray Analysis Apparatus)

The X-ray analysis apparatus according to the present embodiment is configured as above, and operates as follows. First, the user positions the sample S to be measured at a predetermined position in the X-ray measurement system 8 shown in FIGS. 1 and 2.

Next, through the keyboard 10 and/or the mouse 11, the user instructs the CPU 2 to execute the intended measurement method, e.g., focusing-method wide-angle measurement, reflectivity measurement, rocking curve measurement, or another measurement method. The CPU 2 executes measurement software 36 corresponding to the instructed measurement method, and thereby executes one method corresponding to the instruction, from among a plurality of measurement methods made available by the X-ray measurement system 8.

The measurement outputs measurement data from the X-ray measurement system 8, and the data is stored in the measurement data file 40 in the memory unit 5. If the user wishes to observe the measurement data, the user performs an input to indicate as such through the keyboard 10 and/or the mouse 11 shown in FIG. 1. Then, the CPU 2 launches the program 38 for creating a reduced-size image and the icon-creating program 39, generates the respective image data for a reduced-size image 42 and an icon 43 shown in FIG. 6, and displays the reduced-size image 42 and the icon 43 as a joint image 44 on the screen 9a of the display 9. If a plurality of items of measurement data and analysis data exist, a plurality of joint images 44 are displayed in the format of a list on the screen 9*a*.

The user can view the reduced-size images 42 and thereby immediately and accurately establish the data that he/she wishes to see. The user can ascertain the file names appended to the lower position of the reduced-size images 42, and thereby identify the data in a speedier and more accurate manner. The user can also view the icon 43 displayed adjacent to or overlapping with the required reduced-size image 42, i.e., view the reduced-size image 42 and the icon 43 expressing that a mutually corresponding relationship is present, and thereby speedily and accurately establish which analysis software to use to view the measurement data.

When the user, after thus establishing the required data, selects, e.g., mouse-clicks on, the reduced-size image 42 for the corresponding data, the CPU 2 launches the analysis software indicated by the correspondingly displayed icon 43, and displays the measurement data as an image. The user can use this analysis software to perform a predetermined analysis, e.g., background correction, peak correction, smoothing, peak search, qualitative analysis, quantitative analysis, or crystal structure analysis. The user can perform an analysis intentionally using an analysis software other than that indicated by the icon 43 that was displayed as an image.

Once the analysis has thus been performed, the ID information relating to the analysis software in, e.g., the head section of the analysis data shown in Table 2 is overwritten by the ID information corresponding to the analysis that has just been performed. Therefore, if, after the analysis processing has been completed, the processed measurement or analysis data is displayed on-screen as shown in FIG. 6, the icon 43 that is displayed indicates the analysis software that has just been used.

The icon 43 can be intentionally changed by the user. Such an instance makes it possible to perform an analysis specific to that user. In such an instance, the user can again speedily and accurately ascertain the change of analysis software through the icon 43, and can therefore perform an efficient analysis.

In the embodiment above, GlobalFit, 3D Explore, PDXL, and NANO Solver are given as examples of the analysis software of the present invention. A combination of the CPU 2 and the program 38 for creating a reduced-size image is given as an example of reduced-size-image-creating means. A combination of the CPU 2 and the analysis-icon-creating program 39 is given as an example of analysis-icon-creating means. A combination of the CPU 2, an image data generation software (not shown), and a display 9 is given as an example of an image display means.

Other Embodiments

The present invention was described above with reference to a preferred embodiment. However, the present invention is not limited to the embodiment, and a variety of modifications are possible within the scope of the invention set forth in the claims.

For example, the list display shown in FIG. 6 is an example, and it shall be apparent that a list having another desired layout can be displayed. The number of joint images 44 displayed changes according to the number of items of data stored in the memory unit.

The measurement types, specific examples of the names of analysis software, and IDs for the measurement methods shown in Table 1 are merely given by way of example, it being apparent that measurement types, specific examples of the names of analysis software, and IDs for the measurement methods other than those shown can be used as desired.

The file header section shown in Table 2 is also an example, and it shall be apparent that another notation format can be used.

DESCRIPTION OF REFERENCE SYMBOLS

1. X-ray analysis apparatus, 2. CPU, 3. ROM, 4. RAM, 5. memory unit, 8. X-ray measurement system, 9. display (image display means), 9*a*. display screen, 10. keyboard (input means), 11. mouse (input means), 12. data bus, 15. goniometer (angle-measuring instrument), 16. X-ray generation device, 17. X-ray detector, 18. filament, 19. target, 22. incident optical system, 23. reception optical system, 24. monochromator unit, 25. cross-beam optics unit, 26. incident optical unit, 27. incident slit box, 30. first reception slit box, 31. first reception optical unit, 32. second reception slit box, 33. second reception optical unit, 34. attenuator unit, 36. measurement software, 37. analysis software, 38. program for creating a reduced image (reduced-size image-creating means), 39. icon-creating program (analysis-icon-creating means), 40. measurement data file, 41. analysis data file, 42. reduced-size image, 43. icon, 44. joint image, F. X-ray focus (X-ray source), R1. incident X-ray, R2. diffracted X-ray, S. sample, θ. incidence angle, 2θ. diffraction angle

What is claimed is:

1. An X-ray analysis apparatus having a function for enabling a plurality of measurement methods to be implemented, comprising:
   measurement software for implementing each individual measurement method and acquiring X-ray measurement data from X-rays detected due to the implementing of the individual measurement method;
   analysis software for performing a predetermined analysis on the measurement data and acquiring analysis data;
   reduced-size-image-creating means for creating a reduced-size image on the basis of each item of the measurement data and the analysis data;
   analysis-icon-creating means for creating an icon for denoting the analysis software to which the measurement data or the analysis data indicated by the reduced-size image created by the reduced-size-image-creating means corresponds, wherein said measurement data indicates a measurement method under which said measurement data was acquired; and
   image display means for displaying the reduced-size image and the icon on the same screen while indicating that the reduced-size image and the icon are correlated, wherein:
   the X-ray analysis apparatus irradiates a sample with X-rays released from an X-ray source and then detects, by an X-ray detector, a diffracted X-ray, a reflected X-ray or a small-angle-scattered X-ray each given off by the sample; and
   the image display means displays a joint image indicating that a correlation is present between the reduced-size image created by the reduced-size-image-creating means and the icon created by the analysis-icon-creating means, the icon denoting the analysis software to which the measurement data or the analysis data indicated by the reduced-size image corresponds.

2. The X-ray analysis apparatus according to claim 1, wherein displaying the correlation between the reduced-size image and the icon involves (i) displaying the icon adjacent to the reduced-size image, or (ii) having a portion of the icon overlap a portion of the reduced-size image in the display.

3. The X-ray analysis apparatus according to claim 2, wherein the reduced-size image is displayed in accordance with image data created directly on the basis of the measurement data.

4. The X-ray analysis apparatus according to claim 3, wherein the analysis-icon-creating means creates the icon according to information inputted by the user.

5. The X-ray analysis apparatus according to claim 4, wherein the analysis-icon-creating means identifies the analysis software on the basis of an item notated in a file header portion of the measurement data, or an extension on the measurement data; or an item notated in a file header portion of the analysis data, or an extension on the analysis data.

6. The X-ray analysis apparatus according to claim 5, wherein the analysis-icon-creating means identifies the analysis software on the basis of a notation of a measurement method ID recorded in the file header portion of the measurement data or a notation of an analysis software ID recorded in the file header portion of the analysis data.

7. The X-ray analysis apparatus according to claim 5, wherein the analysis-icon-creating means identifies the analysis software on the basis of a measurement condition notated in the file header portion of the measurement data or a measurement condition notated in the file header portion of the analysis data.

8. The X-ray analysis apparatus according to claim 1, wherein the reduced-size image is displayed in accordance with image data created directly on the basis of the measurement data.

9. The X-ray analysis apparatus according to claim 1, wherein the analysis-icon-creating means creates the icon according to information inputted by the user.

10. The X-ray analysis apparatus according to claim 1, wherein the analysis-icon-creating means identifies the analysis software on the basis of an item notated in a file header portion of the measurement data, or an extension on the measurement data; or an item notated in a file header portion of the analysis data, or an extension on the analysis data.

11. The X-ray analysis apparatus according to claim 1, wherein
the plurality of measurement methods are (1) an out-of-plane measurement, (2) an in-plane measurement, (3) a rocking curve measurement, (4) a high-resolution rocking curve measurement, (5) a high-resolution in-plane measurement, (6) a thin-film measurement, (7) a pole figure measurement, (8) a reciprocal space map measurement, (9) a wide-region reciprocal space map measurement, (10) a reflectivity measurement, and (11) a small-angle scattering measurement;
the out-of-plane measurement, the in-plane measurement, the rocking curve measurement, the high-resolution rocking curve measurement, high-resolution in-plane measurement, the thin-film measurement, the pole figure measurement, the reciprocal space map measurement, and the wide-region reciprocal space map measurement each use a diffracted X-ray,
the reflectivity measurement uses a reflected X-ray, and
the small-angle scattering measurement uses a small-angle-scattered X-ray.

12. The X-ray analysis apparatus according to claim 11, wherein the analysis is a background correction, a peak correction, a smoothing, a peak search, a qualitative analysis performed through comparison with a database, or a quantitative analysis.

* * * * *